United States Patent [19]

Abergel et al.

[11] Patent Number: 5,624,434
[45] Date of Patent: Apr. 29, 1997

[54] LASER PREPARATION OF RECIPIENT HOLES FOR GRAFT IMPLANTATION IN THE TREATMENT OF ICEPICK SCARS

[75] Inventors: Robert P. Abergel, Pacific Palisades, Calif.; Michael Slatkine, Herziiah, Israel; Douglass Mead, Allendale, N.J.

[73] Assignee: Laser Industries, Ltd., Tel Aviv, Israel

[21] Appl. No.: 383,074

[22] Filed: Feb. 3, 1995

[51] Int. Cl.$^6$ ................................. A61B 17/36
[52] U.S. Cl. ............................................... 606/9
[58] Field of Search .................... 606/9, 10, 11, 606/12

[56] References Cited

U.S. PATENT DOCUMENTS

| | | | |
|---|---|---|---|
| 3,884,236 | 5/1975 | Krasnov | 128/303 |
| 4,469,098 | 9/1984 | Davi | 128/303.1 |
| 4,566,453 | 1/1986 | Kumano et al. | 128/303.1 |
| 4,587,396 | 5/1986 | Rubin | 219/121 LU |
| 4,672,969 | 6/1987 | Dew | 128/397 |
| 4,733,660 | 3/1988 | Itzkan | 606/9 |
| 4,917,083 | 4/1990 | Harrington et al. | 606/15 |
| 5,071,417 | 12/1991 | Sinofsky | 606/8 |
| 5,207,671 | 5/1993 | Franken et al. | 606/9 |
| 5,280,378 | 1/1994 | Lombardo . | |
| 5,342,352 | 8/1994 | Franken et al. | 606/9 |
| 5,411,502 | 5/1995 | Zair | 606/10 |

OTHER PUBLICATIONS

Sharplan Lasers, Inc. "Silk Touch Transformation" brochure, published in the United States in Jan. 1995, 4 pages.

Sharplan Lasers, Inc. "Advanced Technology for Aesthetic $CO_2$ Laser Surgery" brochure, published in the United States in Jan. 1995, 2 pages.

Sharplan Lasers, Inc. "Sharplan 771 Microscan" brochure, published in the United States in Jan. 1995, 3 pages.

Sharplan Lasers, Inc. "Sharplan 775" brochure, published in the United States in Jan. 1995, 2 pages.

Sharplan Lasers, Inc. "Sharplan 775/776/777 Microscan" brochure, published in the United States in Jan. 1995, 2 pages.

Sharplan Lasers, Inc. "Sharplan 771 General System Description" brochure, published in the United States in Jan. 1995, 17 pages.

Sharplan Lasers, Inc. "Sharplan 775A/B System Description" brochure, published in the United States in Jan. 1995, 23 pages.

Michael Slatkine, PhD, Yosef P. Krespi, MD; *Instrumentation For Office Laser Surgery;* Operative Techniques in Otolaryngology–Head and Neck Surgery, vol. 5, No. 4, Dec. 1994, pp 211–217.

Aesthetic $CO_2$ Laser System literature, Aug. 1994; 2 pages.

R. Rox Anderson and John A. Parrish; *Selective Photothermolysis: Precise Microsurgery By Selective Absorption of Pulsed Radiation;* American Association for the Advancement of Science, 29 Apr. 1983, vol. 220, pp. 524–527.

Andrew Blitze, MD, DDS, *Laser Photocoagulation in the Care of Patients with Osler–Weber–Rendu Disease*, O;erative Techniques in Otolaryngology–Head and Neck Surgery, vol. 5, No. 4, Dec. 1994, pp. 274–277.

Arielle Kauvar, M.D., *Laser Therapy for Cutaneous Vascular Lesions*, "Operative Techniques in Otolaryngology–Head and Neck Surgery, " vol. 5, No. 4, Decl 1994, pp. 250–258.

Richard W. Maloney, MD "Laser Otology", Operative Techniques in Otolaryngology Head and Neck Surgery, vol. 3, No. 2, Jun. 1992, pp 74–83.

(List continued on next page.)

Primary Examiner—Lee S. Cohen
Assistant Examiner—Sonya Harris-Ogugua
Attorney, Agent, or Firm—Cobrin, Gittes & Samuel

[57] ABSTRACT

A method of treating ice pick scars is provided in which the epidermal layer surrounding an ice pick scar is ablated to provide a recipient hole into which skin is grafted. Smoothing of the skin after grafting may then be performed with permanent rejuvenation.

12 Claims, 1 Drawing Sheet

OTHER PUBLICATIONS

I.L. Med. Unilase product info. brochure "The Proven Solution for Disk, Spinal Cord and Brain Microsurgery" (1993).

I.L. Med Unilase product info. brochure "The Proven Solution for Otologic Microlaryngeal Surgery" (1993).

"UNILASE A new $CO_2$ Laser for Microsurgery", I.L. Med. Newsletter, vol. 1, No. 3, Spring 1991.

"New Laser for Microlaryngeal Surgery", I.L. Med Newsletter, vol. 1, No. 1, Spring 1991.

S. George Lesinski, MD and Richard Newrock, Ph.D. "Carbon Dioxide Lasers for Otosclerosis", Otolaryngologic Clinics of North America, vol. 26, No. 3, Jun. 1993.

I.L. Med Unilase System Brochure (1993).

"Using a $CO_2$ Laser During Conventional Microdiskectomy Shows Promise of Faster Recovery", I.L. Med Newsletter, vol. 1, No. 4, Spring 1991.

I.L. Med Magana Diskectomy Microreactor Set, brochure.

"Palm Beach Gardens Medical Center First in Nation to Perform Advanced Laser Back Surgery," press release.

I.L. Med UNILASE CO2 Laser information relating to mounts, balancing and drapes.

I.L. Med Advertisement suggesting use of the CO2 Laser with the new UNILASE.

LASER PREPARATION OF RECIPIENT HOLES FOR GRAFT IMPLANTATION IN THE TREATMENT OF ICEPICK SCARS

BACKGROUND

The present invention relates to the laser preparation of recipient holes for graft implantation assuring minimal thermal damage to the walls of the recipient hole. This method is particularly useful in the treatment of icepick scars.

Ice pick scars, given their depth (generally a crater of 1–5 mm), typically require different methods of treatment than those used for facial depressions. The surgical technique of punch excision followed by full thickness skin grafting is the current treatment of choice for ice pick scars. However, this technique is lengthy due to the various steps involved. The scar is first punched out, and then lifted by forceps and finally cut out by use of scissors. These steps are followed by moderate hemorrhage during the first days of wound healing which sometimes compromises the viability of the grafts, their final positioning and therefore, the cosmetic results for the patient.

SUMMARY OF THE INVENTION

A method of treating an ice pick scar in the skin of a human is disclosed comprising ablating the epidermal layer surrounding the ice pick scar to provide a recipient hole, obtaining a plug of skin having an epidermal and dermal layer from an area of skin other than from said ice pick scar and grafting the plug of skin into the recipient hole providing a grafted area. The method contemplates that the plug which is grafted is from the same patient. After sufficient healing, it may be desirable to smooth the grafted area. A method of smoothing or rejuvinating is thus provided comprising ablating the grafted area to above the papillary dermis with a laser beam.

It is an objective of the present invention to provide a method of treating ice pick scars.

DETAILED DESCRIPTION OF THE INVENTION

Figure 1:
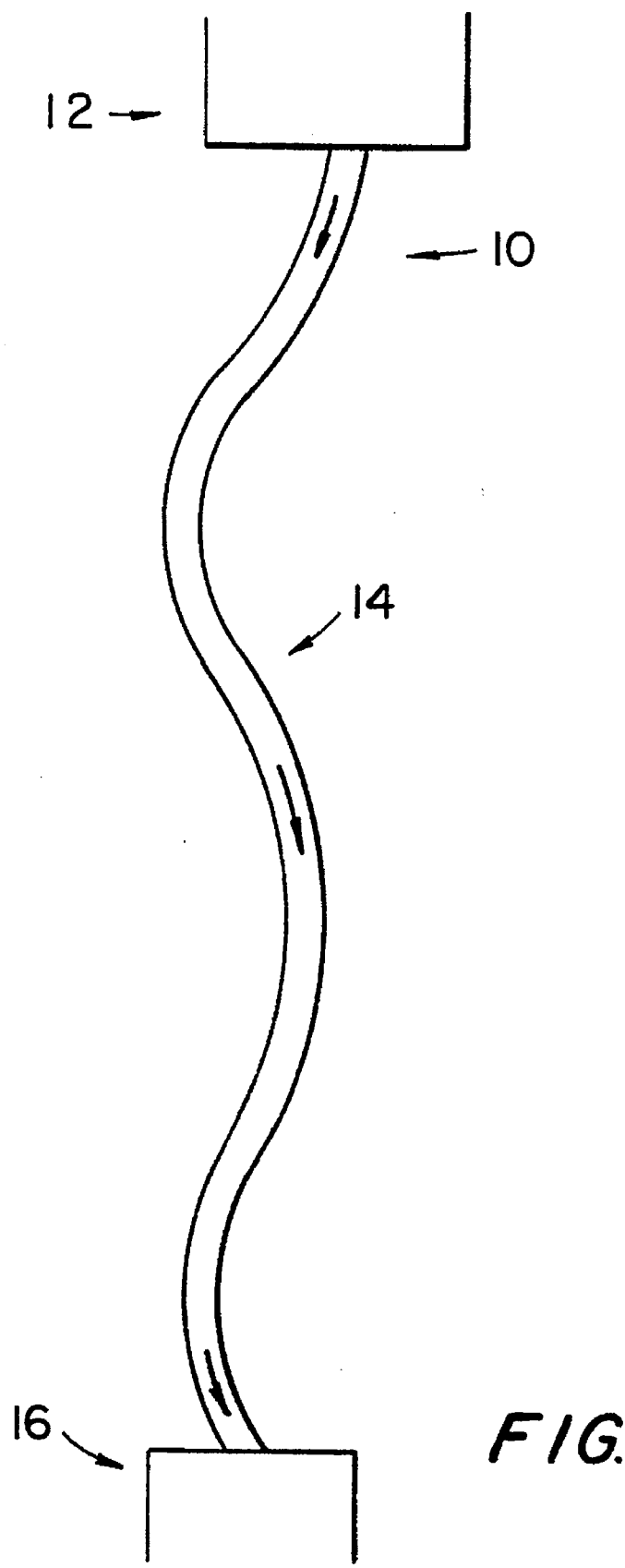
FIG. 1 depicts a fiber through which a laser beam may be emitted.

A laser beam is used in the present invention to ablate the area surrounding an ice pick scar.

A laser is preferably used in conjunction with a flash scanner system. Flash scanner systems are described in U.S. patent application Ser. No. 08/175,980 entitled "A System for Causing Ablation of Irradiated Material of Living Tissue While Not Causing Damage Below a Predetermined Depth" which has been allowed at this writing, and in the U.S. Patent Application filed on Dec. 19, 1994 entitled "Method and Apparatus for Applying Laser Beam to a Working Surface, Particularly for Ablating Tissue" (no U.S. Serial No. issued as yet). The flash scanner system contains reflectors such as mirrors or prisms which are angularly positioned to deflect the laser beam and irradiate in a predetermined pattern. The movements of the reflectors of the flash scanner are generally microprocessor controlled. The carbon dioxide laser is the laser of choice in conjunction with the flash scanner for the uniform ablation of irradiated material. The laser beam of light may be emitted from an articulated arm or, as provided herein, a laser fiber. A focused or slightly defocused beam may be used. The use of a laser with the flash scanner permits all irradiated skin to be ablated with negligible thermal damage and char to the underlying skin. Moreover, any residual thermal damage is shallow and controlled.

Constant velocity of scanning the surface with the laser beam permits homogenous tissue ablation. The beam moves rapidly over the skin, ensuring a 1 millisecond exposure on individual sites within the spot. The beam is focused at 0.2 mm: at a power of 20 watts, it will generate a high power density to generate char free tissue ablation. With such a device, the depth is perfectly controlled and the thermal damage to underlying and adjacent dermis is limited.

Preferably, the beam travels through an optical waveguide before reaching the flash scanner. FIG. 1 depicts such an optical waveguide 10 through which a laser beam may travel. The laser beam is generated at laser source 12 and travels through the optical waveguide 14 in the direction of the arrows to the flash scanner 16 containing the reflector system. The optical waveguide, which is loosely referred to as a fiber, provides superior waveguide capability for the laser beam. It also participates in defocusing the laser beam. After passing through the flash scanner, the laser beam is emitted to irradiate the skin surface (not shown here).

Preparation

After informed consent, the patient's skin was prepared thoroughly in a sterile fashion. Ice pick scars were then identified, marked and measured. The skin was then locally anesthetized by infiltrating with 1% Xylocaine, 1:100 000 epinephrine, and 8.4% sodium bicarbonate. The retroauricular donor site was also prepared and anesthetized.

Laser Scar Irradiation

A continuous wave $CO_2$ laser was used to selectively vaporize the ice pick scar at a power of 20 watts, 0.5 sec exposure. The laser was connected to the reflecting system which provides a predetermined spiral pattern with an 80 mm focusing handpiece, which produces a 150 micron focal spot. A 2 mm diameter scan area was selected.

Flash scanning with a focused beam spot size permits attainment of char fee ablation with very high densities. To selectively remove each scar, a short 0.5 sec pulse can vaporize the tissue with full disintegration and no residues. Approximately 30 scars were vaporized bloodlessly in less than one minute. The depth of penetration was perfectly controlled.

Graft Placement

Full thickness skin grafts of 2.5 mm diameter were then harvested from the donor site. They were then positioned onto the recipient hole and maintained by Masticol™ and sterile guaze for 1 week.

The complete removal of an ice pick scar takes 0.5 seconds. The laser simply disintegrates the scar and the recipient bed is immediately ready for grafting. The bloodless scar vaporization further contributes to the speed of the technique. Additional advantages are evident. The graft will remain properly positioned with the skin as it will not be pushed up by fluid. Also, the absence of blood around the graft will allow a better approximation of the graft with the rest of the patients skin, leading to improved healing. Survival of the grafts should be improved by a bloodless environment.

After sufficient healing of the grafted area, skin rejuvenation or smoothing may be performed by ablating the grafted area to above the papillaary dermis. Further details thereof are provided in a patent application entitled "Laser Facial Rejuvination" filed simultaneously herewith.

What is claimed is:

1. A method for treating an ice pick scar in the skin of a human comprising:

bloodlessly ablating with a laser beam the epidermal and dermal layers surrounding said ice pick scar to provide a recipient hole, said recipient hole having a depth greater than its diameter;

obtaining a plug of skin having epidermal and dermal layers from an area of skin of said human other than from said ice pick scar; and grafting said plug of skin into said recipient hole providing a grafted area.

2. A method as claimed in claim 1 further comprising bloodlessly ablating with a laser beam the epidermal layer of skin of the grafted area to a depth that is above the collagen producing cells of the papillary dermal layer.

3. A method as claimed in claim 2 wherein the step of ablating further comprises emitting said laser beam from a carbon dioxide laser.

4. A method as claimed in claim 2 further comprising passing said laser beam through an optical waveguide to defocus said laser beam prior to ablating said area of said ice pick scar.

5. A method as claimed in claim 2 wherein the step of ablating further comprises scanning said laser beam with a flash scanner system to provide a predetermined spiral pattern on said epidermal layer surrounding said ice pick scar.

6. A method as claimed in claim 5 wherein the step of ablating further comprises ensuring a 1 millisecond exposure time of said laser beam to each individual site within the predetermined spiral pattern on said epidermal layer surrounding said ice pick scar.

7. A method as claimed in claim 2 wherein the step of ablating further comprises emitting a continuous wave $CO_2$ beam as said laser beam.

8. A method as claimed in claim 1 wherein the step of ablating further comprises emitting said laser beam from a carbon dioxide laser.

9. A method as claimed in claim 1 further comprising passing said laser beam through an optical waveguide to defocus said laser beam prior to ablating said area of said ice pick scar.

10. A method as claimed in claim 1 wherein the step of ablating further comprises scanning said laser beam with a flash scanner system to provide a predetermined spiral pattern on said epidermal layer surrounding said ice pick scar.

11. A method as claimed in claim 1 wherein the step of ablating further comprises emitting a continuous wave $CO_2$ beam as said laser beam.

12. A method as claimed in claim 10 wherein the step of ablating further comprises ensuring a 1 millisecond exposure time of said laser beam to each individual site within the predetermined spiral pattern on said epidermal layer surrounding said ice pick scar.

* * * * *